(12) United States Patent
Bowles et al.

(10) Patent No.: US 7,578,159 B2
(45) Date of Patent: Aug. 25, 2009

(54) CONTROLLED CYCLE-LIFE JAW ASSEMBLY

(75) Inventors: Richard R. Bowles, Elyria, OH (US); Paul W. Gress, Elyria, OH (US)

(73) Assignee: Emerson Electric Co., St. Louis, MO (US)

( * ) Notice: Subject to any disclaimer, the term of this patent is extended or adjusted under 35 U.S.C. 154(b) by 178 days.

(21) Appl. No.: 11/575,039

(22) PCT Filed: Sep. 9, 2005

(86) PCT No.: PCT/US2005/031799

§ 371 (c)(1),
(2), (4) Date: Mar. 9, 2007

(87) PCT Pub. No.: WO2006/031548

PCT Pub. Date: Mar. 23, 2006

(65) Prior Publication Data

US 2007/0214859 A1 Sep. 20, 2007

Related U.S. Application Data

(60) Provisional application No. 60/608,191, filed on Sep. 9, 2004.

(51) Int. Cl.
B25B 7/00 (2006.01)

(52) U.S. Cl. ...................... 72/409.01; 72/416

(58) Field of Classification Search ............... 72/31.01, 72/409.01, 409.12, 409.16, 412, 416, 453.15, 72/453.16, 409.19

See application file for complete search history.

(56) References Cited

U.S. PATENT DOCUMENTS

| 3,345,856 | A | * | 10/1967 | Myers et al. ............. 72/409.01 |
| 4,641,877 | A | * | 2/1987 | Merrill ........................ 294/101 |
| 5,279,140 | A | * | 1/1994 | Blake et al. ................ 72/31.01 |
| 5,611,229 | A | * | 3/1997 | Chadbourne et al. ....... 72/31.01 |
| 6,578,430 | B1 | | 6/2003 | Duerr |
| 7,000,448 | B2 | | 2/2006 | Hamm et al. |
| 7,155,955 | B2 | | 1/2007 | Bowles et al. |
| 7,434,440 | B2 | * | 10/2008 | Fay ........................... 72/409.1 |
| 2003/0046973 | A1 | | 3/2003 | Hamm et al. |
| 2004/0154371 | A1 | | 8/2004 | Hamm et al. |

FOREIGN PATENT DOCUMENTS

DE 19918219 C1 1/2001

OTHER PUBLICATIONS

Search Report and Written Opinion for corresponding International Application No. PCT/US2005/031799.

* cited by examiner

*Primary Examiner*—Edward Tolan
(74) *Attorney, Agent, or Firm*—Locke Lord Bissell & Liddell LLP

(57) ABSTRACT

A jaw assembly for use with a crimping tool is described, wherein the assembly includes a jaw arm and a side plate where the side plate is configured to fail in a manner noticeable to a user of the jaw assembly prior to the anticipated failure of the jaw arm. The side plate includes a stress riser, such as a milled slot formed in one face of the sideplate, to ensure such failure.

14 Claims, 10 Drawing Sheets

CONTROLLED CYCLE-LIFE JAW ASSEMBLY

CROSS REFERENCE TO RELATED APPLICATIONS

The present invention is a 35 U.S.C. 371 application of PCT/US2005/031799 filed on Sep. 9, 2005, and claims priority to U.S. Provisional Patent Application Ser. No. 60/608, 191 filed Sep. 9, 2004, the contents of all of which are incorporated herein by reference.

FIELD OF THE INVENTION

The present invention relates generally to a tool for crimping fittings to connect sections of pipe and, more particularly, to an improved jaw assembly for use in crimping such fittings.

BACKGROUND OF THE INVENTION

A compression fitting is typically a tubular sleeve containing seals. The fitting is compressed in radial directions to engage the ends of pipes. The compression fittings form a leak resistant joint between the pipe ends. The joint has considerable mechanical strength and is self-supporting. In order to compress the fitting, a crimping tool is used.

A typical crimping tool includes an actuator and pivoting crimp arms or jaws. The actuator may be a hydraulic actuator that includes a hydraulic cylinder with a piston. The piston includes rollers that contact the crimp arms or jaws. In operation, a hydraulic pump builds up hydraulic pressure in the cylinder to press the piston with its rollers against the arms or jaws. The rollers engage ends of the jaws in line engagement and cause them to pivot and crimp the compression fitting disposed between the jaws.

Depending on the intake angle of the rollers on the ends of the jaws, significant crimping forces may be produced. As a result of these intense forces, the arms or jaws undergo intense forces when crimping and can fail. In many instances failure of the jaws result in a crack or deformation that either prevents further use of the jaw assembly or that is readily visible to the user of the crimping assembly. In such instances, the potential for an incomplete and improper crimp is typically avoided because the jaw assembly cannot be used, or the user of the crimping tool will observe the crack or deformation and thereafter have knowledge that the jaw assembly cannot be relied upon to produce a complete crimp. However, for certain sizes of crimping assemblies, especially for smaller-sized crimping assemblies, there is the potential that the failure of one or both of the jaws could result in a crack occurring in the jaws that does not render the jaw assembly unusable and that is not readily observable by a user of the assembly. Under such circumstances, there is the potential that the user of the crimping assembly will continue to make crimps with the cracked jaw assembly, potentially leading to inferior or incomplete crimps. Such inferior or incomplete crimps are undesirable.

The present disclosure is directed to an improved jaw assembly that will tend to inhibit or avoid the occurrence of a condition where a cracked jaw occurs and/or continues to be used for crimping operations.

SUMMARY OF THE DISCLOSURE

The present disclosure is directed to an improved jaw assembly that will tend to inhibit or avoid the occurrence of a condition where a cracked jaw occurs and/or continues to be used for crimping operations. In accordance with certain teachings of this disclosure a jaw assembly is described for use with a crimping tool that includes at least one jaw arm and a sideplate coupled to the jaw arm, where the sideplate includes a stress riser to ensure that the sideplate fails in a manner noticeable to a user of the jaw assembly prior to the anticipated failure of the jaw arm. In a further embodiment, the stress riser comprises a milled slot with a sharp corner formed in the sideplate. In yet another embodiment, the stress riser comprises a slot formed in the sideplate, wherein the slot extends across pivot pin openings in a face of the sideplate.

In another embodiment of the present invention, a crimping tool assembly that includes a first jaw member and a second jaw member, first and second pivot pins, and at least one sideplate having pivot pin openings is described, wherein the first and second jaw members are oriented opposite to each other, the first and second jaw members are coupled to the sideplate through first and second pivot pins, and the sideplate includes a stress riser to ensure that the sideplate fails in a manner noticeable to a user of the jaw assembly prior to the anticipated failure of the jaw arm. In a further embodiment, the stress riser comprises a slot with a sharp corner formed in the sideplate. In yet another embodiment, the stress riser comprises a slot that extends across pivot pin openings in a face of the sideplate.

BRIEF DESCRIPTION OF THE DRAWINGS

The foregoing summary, description of a preferred embodiment, and other aspects of the present invention will be best understood with reference to a detailed description of specific embodiments of the invention, which follows, when read in conjunction with the accompanying drawings, in which.

Figure 1:
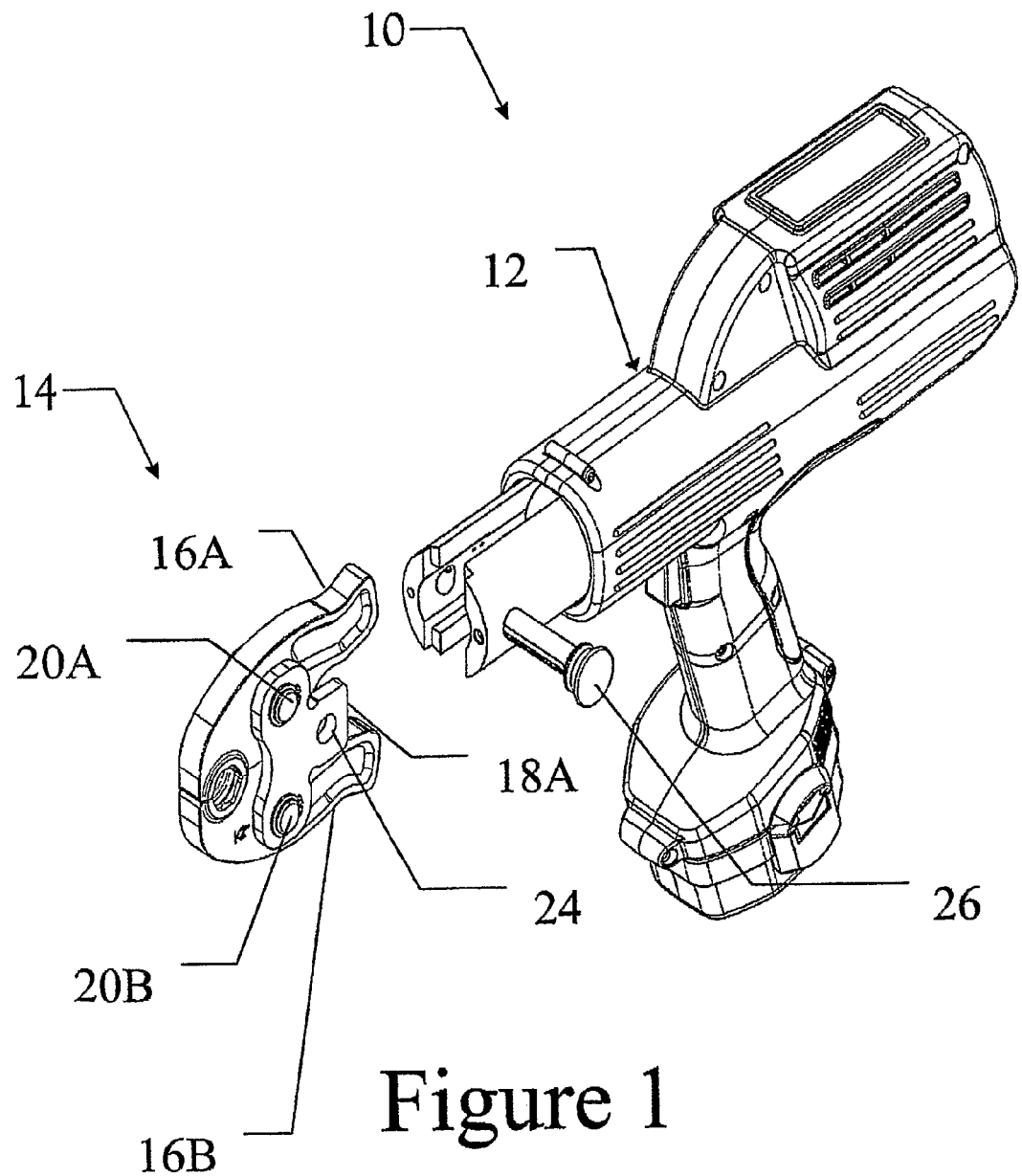
FIG. 1 generally illustrates an exemplary crimping tool assembly 10, including a crimping tool 12 and a jaw assembly 14, constructed in accordance with certain teachings of the present disclosure.

While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the scope of the invention as defined by the appended claims.

DETAILED DESCRIPTION OF THE INVENTION

One or more illustrative embodiments incorporating the invention disclosed herein are presented below. Not all features of an actual implementation are described or shown in this application for the sake of clarity. It is understood that in the development of an actual embodiment incorporating the present invention, numerous implementation-specific decisions must be made to achieve the developer's goals, such as compliance with system-related, business-related, government-related and other constraints, which vary by implementation from time to time. While a developer's efforts might be complex and time consuming, such efforts would be, nevertheless, a routine undertaking for those of ordinary skill in the art having the benefit of this disclosure.

In general terms, Applicants have conceived of and developed devices and methods that utilize sideplates associated with compression assembly, such as crimping tools, having stress risers formed into them, such stress risers including but not limited to slots, partial slots, and geometric disruptions, so as to ensure that the sideplate fails in a manner noticeable to a user of the compression assembly. The devices and methods include original equipment for use with compression assemblies, as well as retrofit equipment to modify existing compression assemblies and devices.

Figure 2:
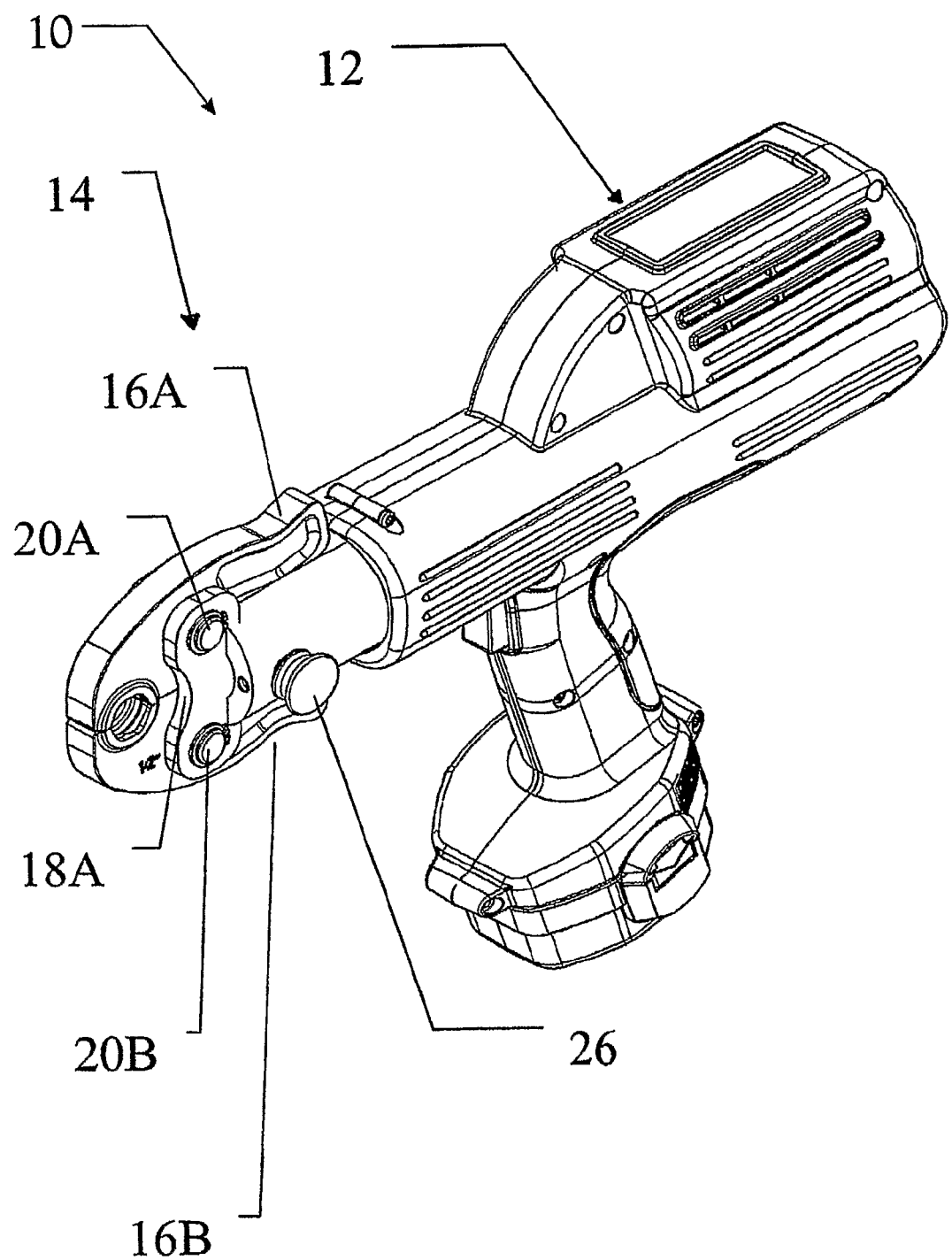
FIG. 2 generally illustrates the exemplary crimping tool assembly 10 of FIG. 1, showing jaw assembly 14 removably attached to crimping tool 12 by retaining pin 26.

Turning to the drawings and, in particular, to FIGS. 1 and 2, an exemplary crimping tool assembly 10 is illustrated. The assembly 10 includes a crimping tool 12 and a jaw assembly 14.

The crimping tool 12 comprises a generally gun-shaped device that includes a hydraulically actuated piston assembly (not shown in FIG. 1 or 2) that is used to actuate the jaw assembly 14 in a manner known to of ordinary skill in the art. The crimping tool 12 can be battery or cord powered. Examples of known crimping tools that may be used to practice the subject matter of the present disclosure include the Model CT-400 and Model 320-E crimping tools available from Ridge Tool Company (Elyria, Ohio).

The jaw assembly 14 includes first and second jaw members or arms 16A and 16B that are coupled together via first and second sideplates 18A and 18B (only sideplate 18A is visible in FIGS. 1 and 2). The jaws 16A and 16B are coupled to the sideplates 18A and 18B through first and second pivot pins 20A and 20B positioned in pivot pin openings 21A, 21B, 21C and 21D defined by the sideplates 18A and 18B. The pivot pins are held in place through the use of retaining rings 22A, 22B, 22C and 22D). As reflected in FIG. 1, the side plates 18A and 18B define an opening 24 for receiving a retaining pin 26 for coupling (e.g., rotatably coupling) the jaw assembly 14 to the crimping tool 12 as it is illustrated in FIG. 2. A spring assembly 19 (depicted in FIG. 4) can be used to bias the jaws open. The jaws may be constructed in accordance with the teachings of published United States Patent Application No. 20040154371, "Compression Tool Jaw Member" and/or United States Patent Application No. 20030046973, "Crimping Assembly", which are hereby incorporated by reference.

Figure 3:
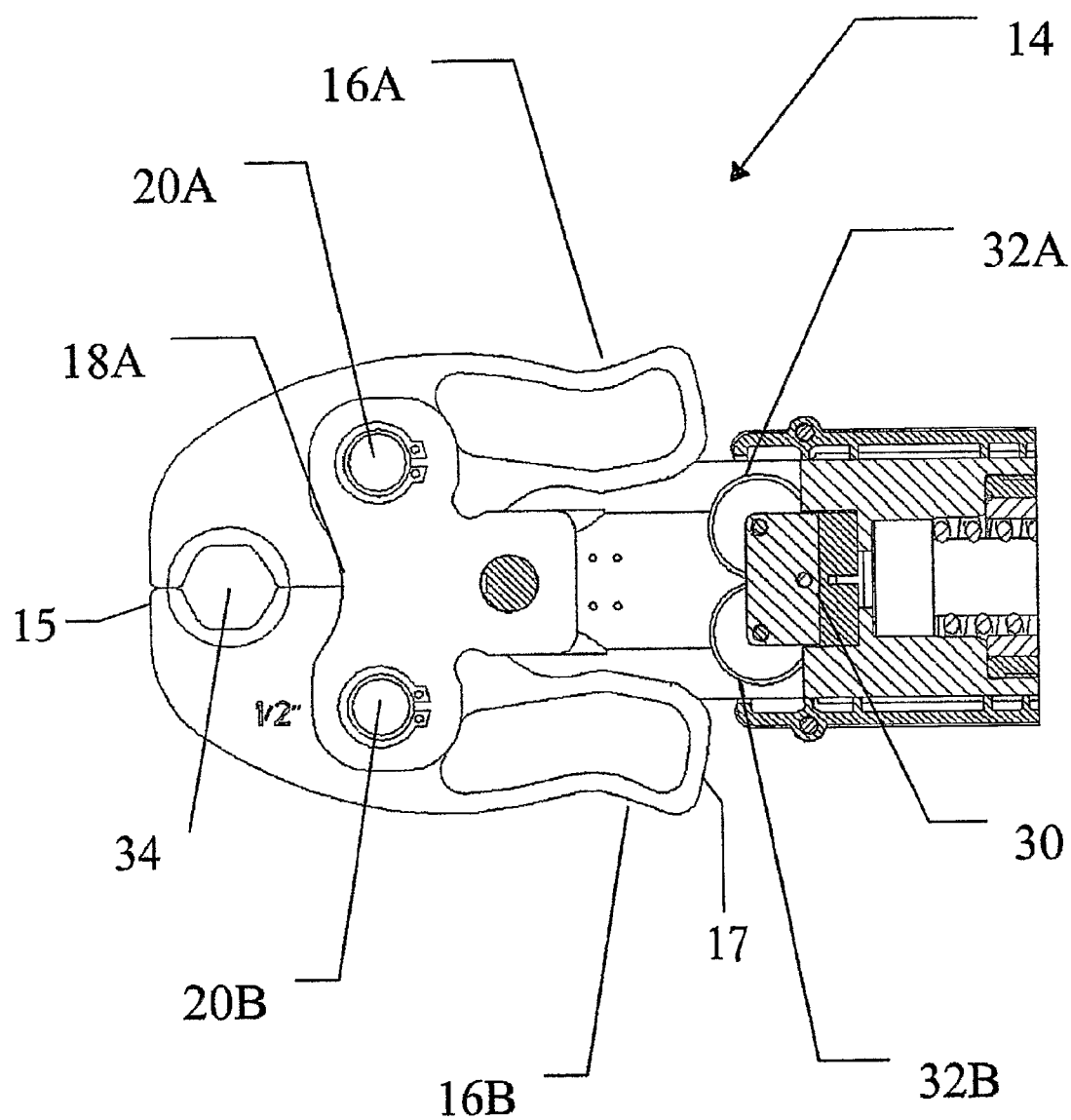
FIG. 3 generally illustrates a side cutaway view of the assembly 10 depicted in FIGS. 1 and 2.

FIG. 3 generally illustrates a side cutaway view of the assembly 10 depicted in FIGS. 1 and 2. As reflected in the figure, the jaw assembly 14 defines at its peripheral end 15 an opening 34 that is sized and shaped to engage a crimp fitting and to result in a crimping of such fitting when the jaw assembly 14 is actuated. As further reflected in the figure, the crimping tool 12 includes a hydraulically actuated piston assembly 30 that includes rollers 32A and 32B. When the crimping tool 14 is activated, e.g., through the depression of a trigger or switch, the hydraulically activated piston assembly 30 will be moved towards the jaw assembly 14 along a path of travel (illustrated by the arrow) causing the rollers 32A ad 32B to engaged the distal end 17 of the jaws 16A and 16B, resulting in a closing of the jaws 14A ad 14B and, if a crimp fitting was positioned in opening 34, a crimping of the fitting.

The application of pressure by the hydraulically activated piston assembly 34 on the jaws 16A ad 16B, and the resultant pressures placed on the jaws by their contact with any crimp fitting within opening 34, results in the application of significant stresses and pressures on the jaw arms 16A and 16B. Over time there is the potential for the jaws 16A and/or 16B and/or the sideplates 18A and/or 8B to fail.

Failure of the jaws 16A and 16B typically results in a crack forming in the jaws and/or deformation of the jaws. In many instances failure of the jaws results in a crack or deformation that either prevents further use of the jaw assembly or that is readily visible to the user of the crimping assembly 10. In such instances, the potential for an incomplete and improper crimp is typically avoided because the jaw assembly 14 cannot be used or the user of the crimping tool will observe the crack or deformation and thereafter have knowledge that the jaw assembly 14 cannot be relied upon to produce a complete crimp. For certain sizes of crimping assemblies 10, especially for smaller sized crimping assemblies 10, there is the potential that the failure of one or both of the jaws 16A or 16B could result in a crack occurring in the jaws 16A or 16B that does not render the jaw assembly 14 unusable and that is obstructed from the view of a user of the assembly because the crack is fully or partially hidden from view by one or more of the sideplates 18A or 18B. Under such circumstances, there is the potential that the user of the crimping assembly will continue to make crimps with the cracked jaw assembly 14, potentially leading to inferior or incomplete crimps. Such inferior or incomplete crimps are undesirable.

In accordance with one embodiment of the present disclosure, undesirable, inferior or incomplete crimps are reduced or avoided through the use of side plates 18A and 18B that are specially constructed to fail in an obvious and visible way before any reasonably anticipated failures of the jaws 16A and 16B.

In one embodiment it was determined that the anticipated cycle life for the sideplates used in a jaw assembly constructed in accordance with certain teachings of this disclosure should be between about 50% and about 80% of the minimum reasonably anticipated cycle life for the jaw arms. Thus, for a jaw assembly having jaw arms with anticipated cycle lifes that exceed 10,000 cycles, the desired cycle life for the side plates would be between about 5,000 to about 8,000 cycles. Such a cycle life range would tend to ensure that the side plate always failed before the jaw arms failed, and would also tend to ensure that the jaw assembly had an appropriate cycle life.

Figure 4:
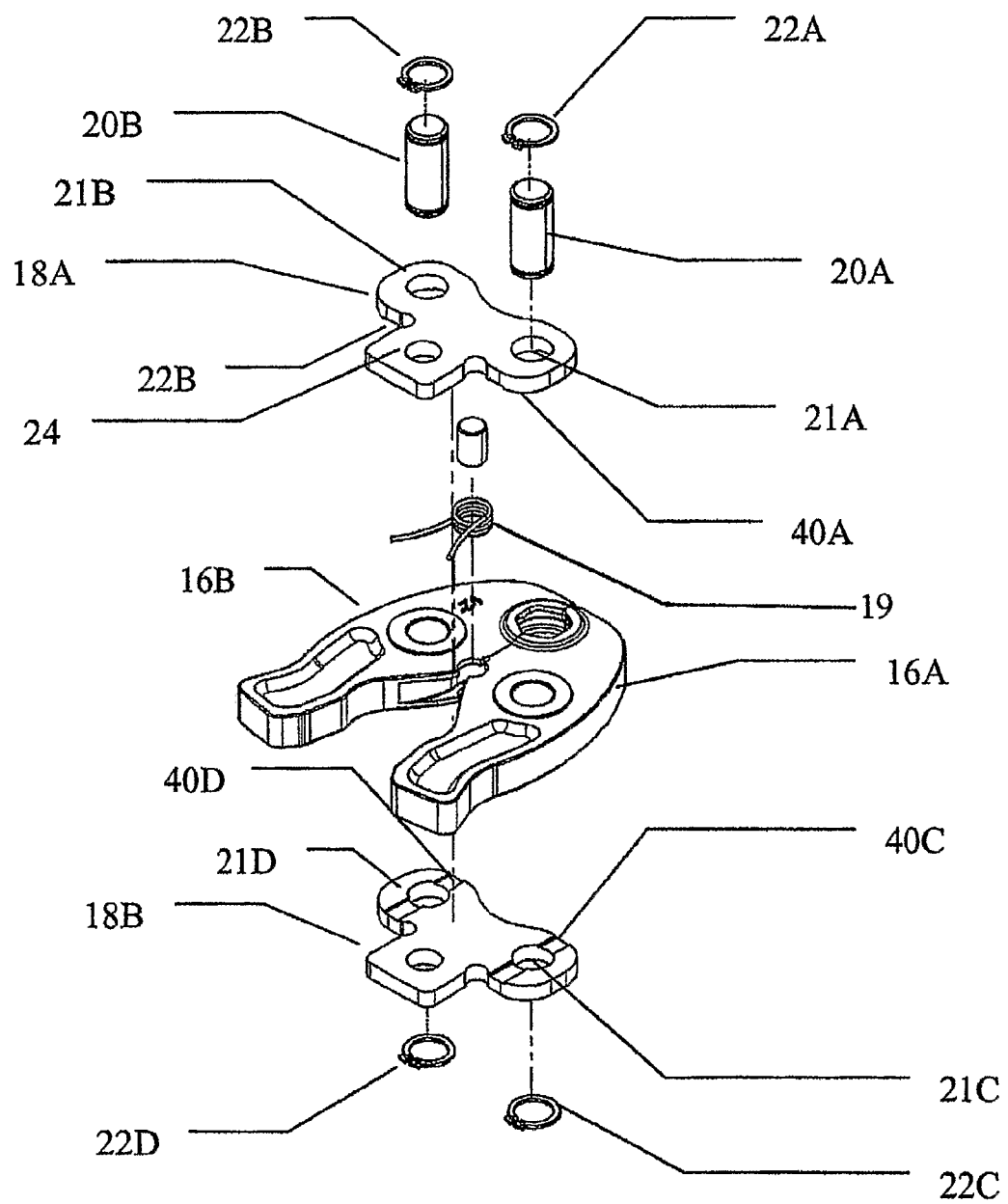
FIG. 4 illustrates an exploded view of a crimping jaw assembly 14 in accordance with an embodiment of a sideplate according to the present invention.
Figure 5A:
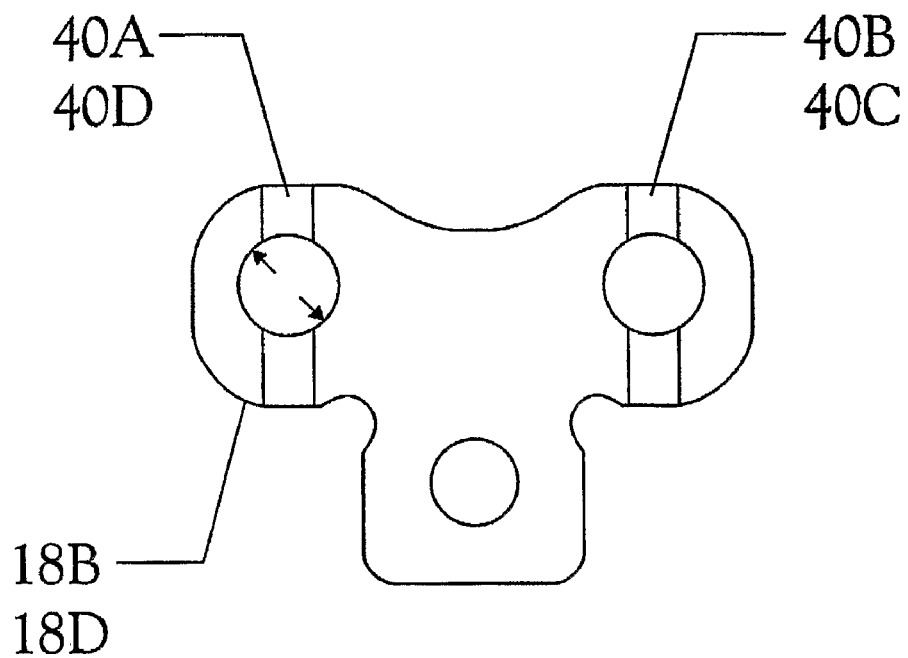
FIG. 5A generally illustrates a top-view of a sideplate having milled slot stress risers 40A-40D completely crossing over the pivot pin openings, in accordance with an aspect of the present invention.
Figure 5B:
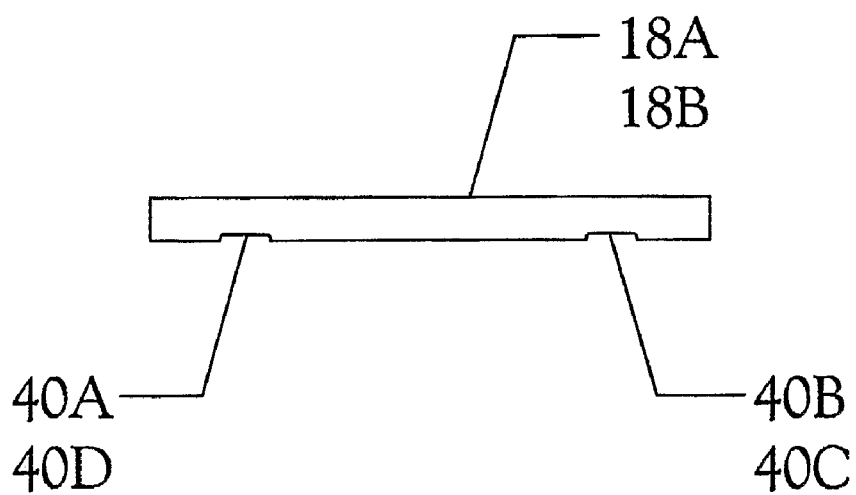
FIG. 5B illustrates a side view of the sideplate of FIG. 5A.

One exemplary jaw assembly that achieves the above goal of a sideplate that will fail in an obvious and visible way prior to anticipate failures of the jaws 16A and 16B is depicted in FIGS. 4 and 5A and 5B. As depicted in the figures, the sideplates 18A and 18B are formed with engineered stress risers, in the form of sharp corner milled slots 40A, 40B, 40C and 40D, being located on one side (or face) of the sideplates. In the illustrated embodiment, the dimensions and positioning of the milled slots 40A-40D, were selected to ensure that the side plates would crack or fail prior to anticipated fatigue failures of the jaw arms 16A and 16B.

In the exemplary embodiment of FIGS. 4 and 5, the side plates 18A and 18B are constructed from steel, such as fine blanked X 42 $NiCrMo_4$, 6 mm thick steel material that is blanked to form the sideplate and then milled, using known milling techniques, to produce the slots 40A-40D. Other materials and methods known to those of skill in the art can be used to produced sideplates 18A and/or 18B. Other materials suitable for use in constructing sideplates 18A and 18B include but are not limited to hot working steels such as CrMoV, CoCrWV, NiCrMoV, NiCrTi, WCrV, and the like; cold working steels including X100 CrMoV; MnCrMo steels, such as 21 $MnCrMo_4$ Grade steel; stainless martensitic steels; stainless ferritic/Austenitic steels; stainless Austenitic steels; cobalt-based alloys; high-temperature Austenitic steels, and combinations thereof. As an example, the sideplates may be roughly 2.008" wide and 1.083" high.

As will be noted in FIGS. 4 and 5, in the exemplary embodiment of FIGS. 4 and 5 the milled slots 40A-40D are positioned such that they cross the pivot pin openings. This is because it was discovered that, in the absence of stress risers, sideplate failures for jaw assemblies as depicted in FIGS. 4 and 5 typically occur when repeated cycling of the jaw assembly results in the development of a fatigue crack that initiates at the pivot pin opening and propagates (up or down) until the part ultimately fractures. By positioning the milled slot stress risers 40A-40D such that they partially or, as illustrated, completely, cross over the pivot pin openings, which is the region where cracks naturally tend to initiate, it is possible to control when and where the cracks begin and thus construct a side plate that will fail in a noticeable and visible way within a relatively narrow band of operating cycles, which is beneficial in ensuring that the sideplate will fail prior to any reasonably anticipated failure of the jaw arms 16A and 16B.

Figure 6:
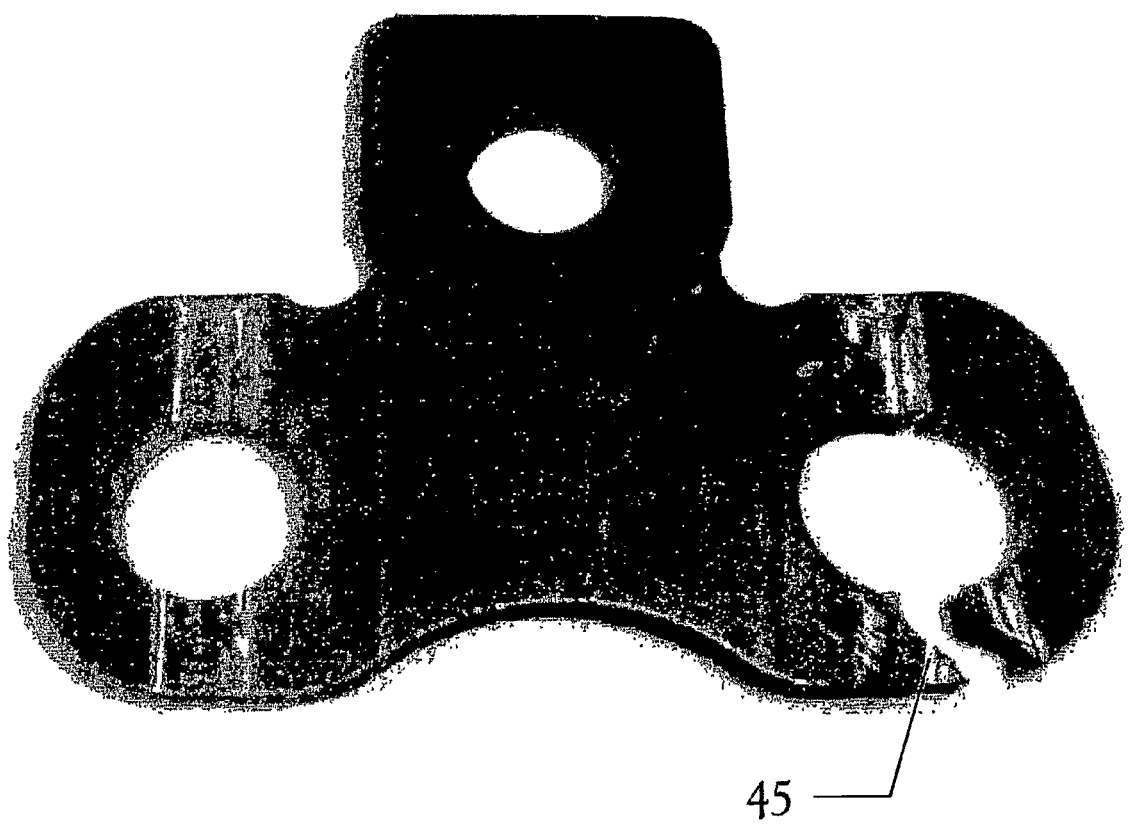
FIG. 6 generally illustrates a sideplate with milled slots in accordance with an aspect of the present invention that has failed in an obvious and visible way prior to anticipated failures of the jaws used in an assembly.

In general, the repeated use of a jaw assembly having a side plate as depicted in FIGS. 4, 5A and 5B will result in the failure of the side plate in an obvious and visible way. As one example, FIG. 6 illustrates a side plate, with milled slots, that has failed. As may be noticed, the inclusion of the milled slots has resulted the failure producing a large and visible crack 45.

While the use of stress risers in the form of milled slots 40A-40D is, in general, beneficial, it has been discovered that additional benefits can be obtained by controlling the depth and width of the slots. As one example it has been discovered that variations in the depth and width of the milled slots can produce different expected useful lifes for the sideplates and different bands over which the sideplates can be expected to fail.

From analysis, it was determined that, for a sideplate constructed with the dimensions and material compositions described above in connection with FIG. 5, the target stress to obtain a desired cycle life of between 5,000 to 8,000 cycles was in the range of 350,000 to 380,000 psi. Based on this analysis, several different slot sizes were tested.

Figure 7:
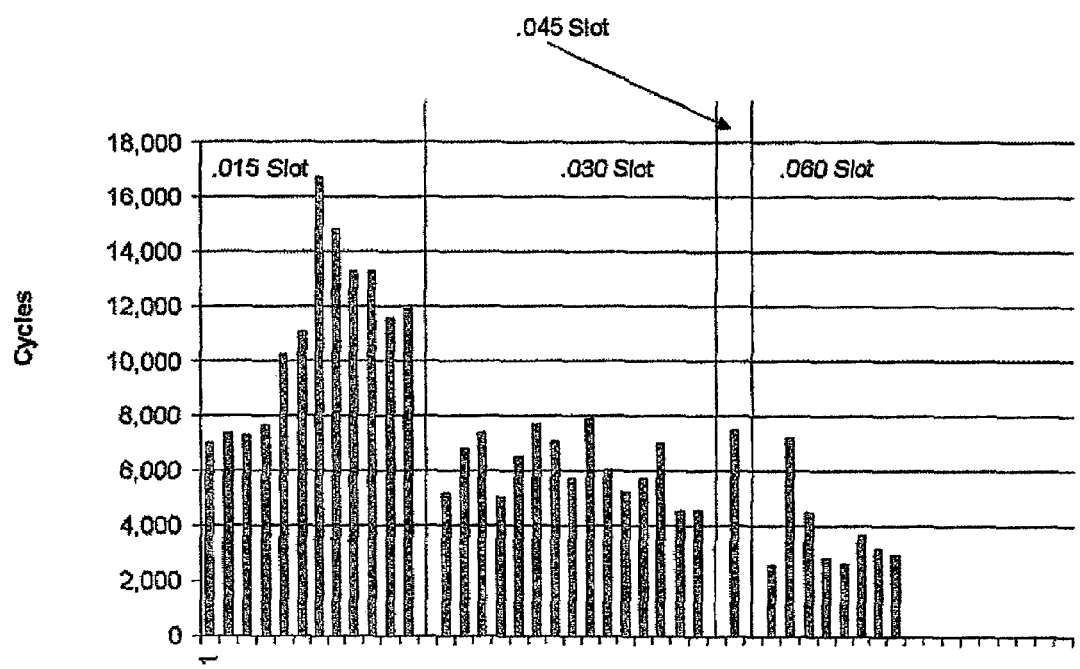
FIG. 7 generally illustrates life cycle tests for jaw assemblies constructed in accordance with certain teachings of this disclosure.

FIG. 7 generally illustrates life cycle tests for jaw assemblies constructed with differing sizes milled slots 40A-40D. Specifically, FIG. 7 reflects life cycles for jaw assemblies having: (a) a slot 0.015" deep×0.250" wide (labeled "0.015 Slot"); (b) a slot 0.030" deep×0.276 wide (labeled "0.030 Slot"); (c) a slot 0.045" deep×0.276 wide (labeled "0.045 Slot"); (d) a slot 0.060" deep×0.276 wide (labeled "0.045 Slot"). In general, these slot sizes were selected based on commonly available milling tooling.

As reflected in FIG. 7, the dimensions of the milled slots can have a significant impact on the life cycle characteristics of the side plate assembly. For example, sideplates formed with the 0.015 Slot slots initially failed within a reasonably narrow range of 7,023 cycles to 7,661 cycles. However, as more sideplates were formed from the tooling and those sideplates were tested, the cycle life of the parts begin to increase and, ultimately, reach and exceed 16,000 cycles, which would not necessarily provide the desired degree of separation between the anticipated cycle life of the sideplate and the anticipate cycle life of the jaw arms. This increase in the anticipated cycle life of the sideplates suggested that the milling currently used to form the slots was wearing out. As long as the corner radius defining the edges of the slots was held to less than about 0.004", cycle life was within a desirable and relatively narrow range. As the cutting tool was subject to wear and the radius increased, the cycle life of the side plates increased as well. This attribute is not necessarily desirable from a manufacturing standpoint.

As further reflected in FIG. 7, an increase in the dimensions of the slot to those of the 0.030 Slot produced different results. In particular, it was found that use of a 0.030 Slot resulted in the production of sideplates that all failed within a relatively narrow and desirable cycle life band of between 4,536 and 7,904 cycles. Moreover, because of the deeper slots, variations in the corner radius that defined the edges of the slots that result from wear on the milling cutter used to form the slots did not necessarily result in substantial variations on the anticipated cycle life. This indicates that the 0.030 design was a more easily and consistently manufacturable design and would be less sensitive to cutter wear than the 0.015 Slot design. Life cycle data for the 0.045 and 0.060 Slots is also provided in FIG. 6.

While the above example indicates that variations in the corner radius of the milled slots can be tolerated, in general, it is desirable to ensure that the corner radius is as small as practical and that the slots have a tight or sharp corner.

It should be understood that the slot dimensions and cycle life results reflected in FIG. 7 are exemplary only and reflect the life cycles for side plates having dimensions and material parameters similar to the side plate generally illustrated in FIGS. 4, 5A and 5B. Sideplates having different overall dimensions, or different material compositions, will likely produce different cycle lifes for different slot dimensions. However, the process described above, of testing different dimensions and multiple side plates, may be used to determine the desirable slot dimensions for a side plate of given dimensions and material composition.

Figure 8A:
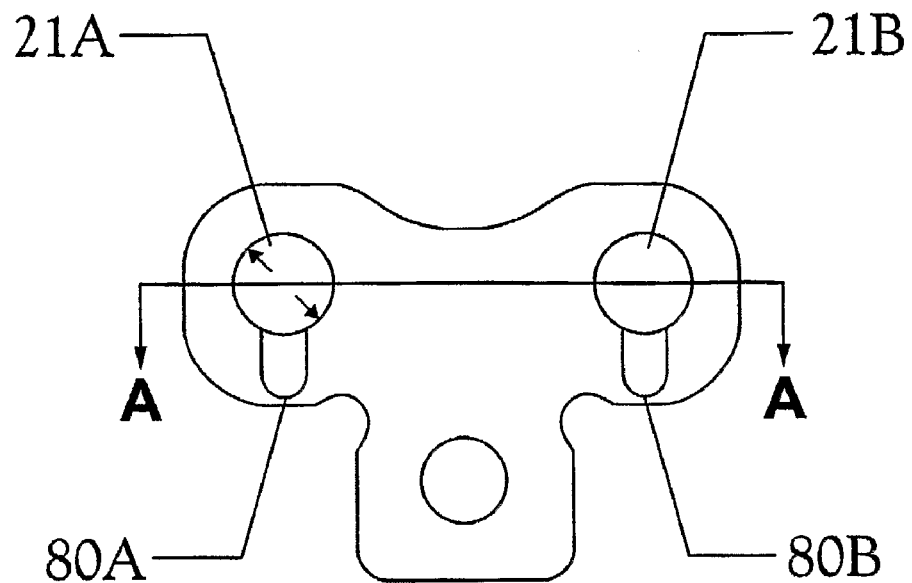
FIG. 8A generally illustrates an alternate embodiment of a sideplate with partial slots that extend in only one direction from pivot pin openings are provided as stress risers.
Figure 8B:
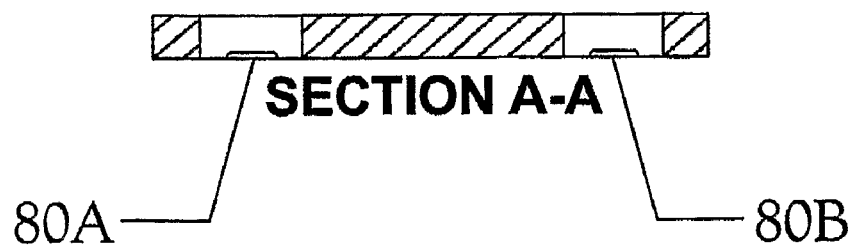
FIG. 8B generally illustrates a sideview of the sideplate of FIG. 8A, taken along line A-A.

It should be understood that the milled slots discussed above are but one approach that can be taken to introduce stress risers in the sideplates to ensure that the sideplates experience a visibly noticeable failure prior to the anticipated failure of the jaw arms. Other approaches can accomplish the same result. One such alternate approach would be to adjust the softness of the material from which the sideplates are formed to ensure appropriate failure of the sideplates. Another approach would be to use slots (milled or otherwise) that are not the full slots described above, but are partial slots that extend in only in one direction from the pivot pin openings. One example of a such an alternate design is provided in FIGS. 8A and 8B, showing partial slots 80A and 80B extending in only 1 direction outward from pivot pin openings 21A and 21B on a face of a sideplate.

Still further alternate embodiments are envisioned that do not require milling operations, but where the stress risers are formed via a stamping or fine blanking process. For example, holes, openings or depressed scribed lines could be placed on the sideplates during a fine blanking procedure (in the location described above in connection with the milled slots or another location) to achieve the desired cycle life for the sideplates. Examples of alternate embodiments along these lines may be found in FIGS. 9 and 10.

Figure 9:
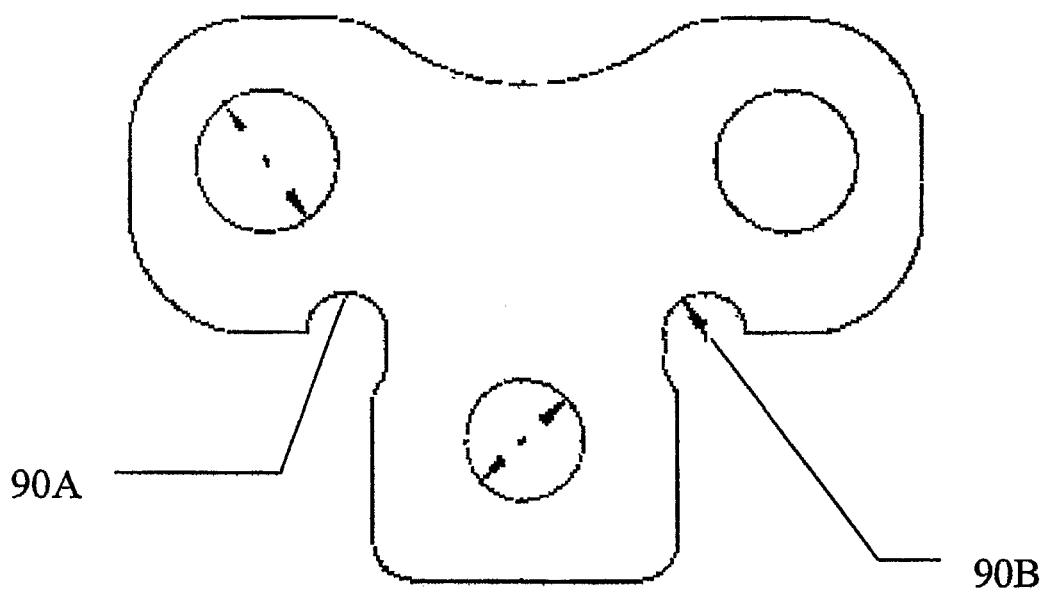
FIG. 9 generally illustrates an alternate sideplate design where corner radii are adjusted and controlled to achieve the desired cycle life.
Figure 10A:
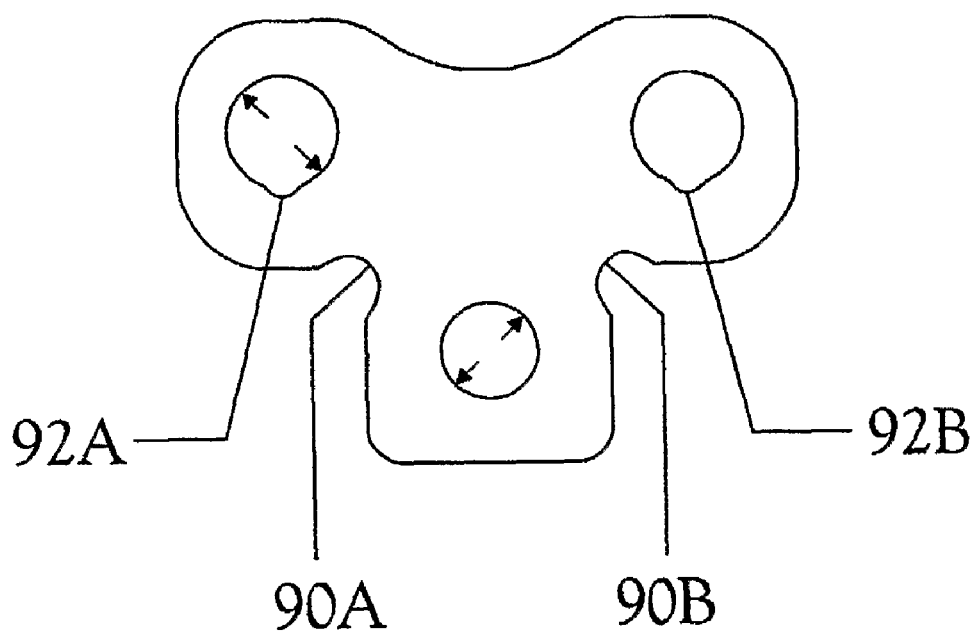
FIG. 10A generally illustrates yet another alternate sideplate design where a fine blanking process is used to create pivot pin openings that are not round, but have small disruptions that act as stress risers.
Figure 10B:
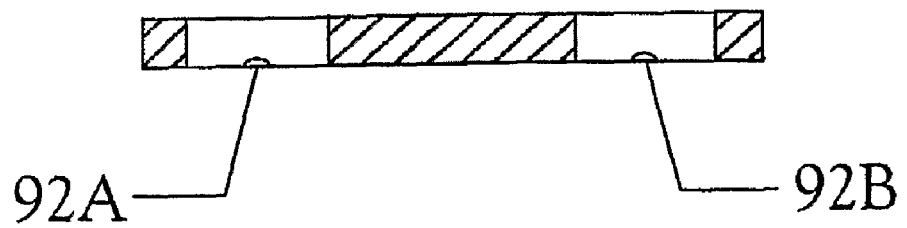
FIG. 10B generally illustrates a sideview of the sideplate of FIG. 10A.

FIG. 9 generally illustrates an alternate sideplate design where the corner radii 90A and 90B are adjusted and controlled to achieve the desired cycle life. FIGS. 10A and 10B generally illustrate a design where a fine blanking process is used to create pivot pin openings that are not round, but rather have openings that are, in general, circular, but that have small geometric disruptions 92A and 92B that act as stress risers. Such geometric disruptions 92A and 92B, while illustrated in FIG. 10A as being generally semi-circular in shape, can be of any appropriate shape desired in order to act as stress risers.

Other techniques, such as reducing the overall thickness of the sideplates (e.g., from 6 mm to 5 mm) could be used to introduce stress risers. Still further, combinations of the above approaches (e.g., the use of fine blanked pivot pin openings as depicted in FIGS. 10A and 10B in combination with scribed lines in the location described above for the milled slots) could be used.

The above discusses the use of side plates with engineered stress risers to ensure sideplate failure before jaw arm failure for jaw assemblies. In addition to, or in place of, ensuring such initial sideplate failure through engineering of the sideplates, it may be possible to ensure that the sideplates fail first by extending the anticipated cycle life of the jaw arms used in the jaw assembly. Approaches for extending the cycle life of the jaw arms include adjusting the dimensions or material of the jaw arms and/or subjecting portions of the arm most prone to fatigue to shot peening. As one example, it was discovered that shot peening could increase the anticipated cycle life of jaw arms by as much as 2,000 to 5,000 cycles.

While the various embodiments of the present invention disclosed herein have been described with reference to the preferred embodiments, it will be appreciated that obvious modifications and alterations are possible by those skilled in the related art. Therefore, it is intended that the invention include all such modifications and alterations to the full extent that they come within the scope of the following claims or the equivalents thereof.

What is claimed is:

1. A jaw assembly for use with a crimping tool, the jaw assembly comprising:
    a first jaw arm member and a second jaw arm member oriented opposite each other and having an anticipated life cycle; and
    a sideplate having at least one pivot pin opening therethrough coupled to the first and second jaw arm members through a pivot pin positioned in the pivot pin opening defined by the sideplate and held in place through at least one retaining ring,
    wherein the sideplate includes a stress riser to ensure that the sideplate fails in a manner noticeable to a user of the jaw assembly prior to an anticipated failure of a jaw arm, and
    wherein the stress riser comprises a slot formed in one side or face of the sideplate.

2. The jaw assembly of claim 1, wherein the slot completely crosses over the pivot pin opening.

3. The jaw assembly of claim 1, wherein the slot is a partial slot extending outwardly from the pivot pin opening.

4. The jaw assembly of claim 1, wherein at least one pivot pin opening in the sideplate has a geometric disruption that acts as a stress riser.

5. The jaw assembly of claim 1, wherein the sideplate is constructed from milled steel.

6. The jaw assembly of claim 1, wherein the sideplate has a life cycle between about 50% and about 80% of the anticipated life cycle for the jaw arm.

7. The jaw assembly of claim 6, wherein the life cycle of the sideplate ranges from about 5,000 cycles to about 8,000 cycles.

8. A crimping tool assembly, the assembly comprising:
    a jaw assembly comprising a first jaw member and a second jaw member, wherein the first and second jaw members have an anticipated life cycle and are oriented opposite each other;
    first and second pivot pins; and
    at least one sideplate having at least one pivot pin opening coupled to the first and second jaw members through first and second pivot pins positioned in the pivot pin opening defined by the sideplate and held in place through at least one retaining ring,
    wherein the at least one sideplate includes a stress riser to ensure that the sideplate fails in a manner noticeable to a user of the jaw assembly prior to an anticipated failure of the jaw arm, and
    wherein the stress riser comprises a slot formed in one side or face of the sideplate.

9. The jaw assembly of claim 8, wherein the slot completely crosses over the pivot pin opening.

10. The jaw assembly of claim 8, wherein the slot is a partial slot extending outwardly from the pivot pin opening.

11. The jaw assembly of claim 8, wherein the at least one pivot pin opening has a geometric disruption that acts as a stress riser.

12. The jaw assembly of claim 8, wherein the sideplate has a life cycle between about 50% and about 80% of the anticipated life cycle for the first and the second jaw members.

13. The jaw assembly of claim 8, wherein the sideplate is constructed from NiCrMo steel material.

14. The jaw assembly of claim 8, wherein the sideplate is constructed from steel material selected from the group consisting of fine blanked X $42NiCrMo_4$, CrMoV, CoCrWV, NiCrMoV, NiCrTi, WCrV, X100 CrMoV, MnCrMo steels, stainless martensitic steels, stainless ferritic/Austenitic steels, stainless Austenitic steels, cobalt-based alloys, high-temperature Austenitic steels, and combinations thereof.

* * * * *